(12) United States Patent
Olson et al.

(10) Patent No.: US 9,555,157 B2
(45) Date of Patent: Jan. 31, 2017

(54) METHOD OF INDUCING HEMOSTASIS IN A WOUND

(71) Applicant: St. Teresa Medical, Inc., Woodbury, MN (US)

(72) Inventors: Curtis Olson, St. Paul, MN (US); Tim Floyd, Eagle, ID (US); Phil Messina, Woodbury, MN (US)

(73) Assignee: St. Teresa Medical, Inc., Eagan, MN (US)

( * ) Notice: Subject to any disclaimer, the term of this patent is extended or adjusted under 35 U.S.C. 154(b) by 0 days.

(21) Appl. No.: 14/539,351

(22) Filed: Nov. 12, 2014

(65) Prior Publication Data

US 2015/0132361 A1    May 14, 2015

Related U.S. Application Data

(60) Provisional application No. 61/903,100, filed on Nov. 12, 2013.

(51) Int. Cl.
| | | |
|---|---|---|
| *A61L 26/00* | (2006.01) | |
| *A61L 15/28* | (2006.01) | |
| *A61L 15/44* | (2006.01) | |
| *A61L 15/60* | (2006.01) | |

(52) U.S. Cl.
CPC .......... *A61L 26/0066* (2013.01); *A61L 15/28* (2013.01); *A61L 15/44* (2013.01); *A61L 15/60* (2013.01); *A61L 26/008* (2013.01); *A61L 26/0023* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 5,447,423 A | 9/1995 | Fuisz et al. | |
| 6,116,880 A | 9/2000 | Bogue et al. | |
| 6,753,454 B1 | 6/2004 | Smith | |
| 6,762,336 B1 | 7/2004 | MacPhee et al. | |
| 6,821,479 B1 | 11/2004 | Smith et al. | |
| 7,019,191 B2 | 3/2006 | Looney | |
| 7,067,444 B2 | 6/2006 | Luo et al. | |
| 7,101,862 B2 | 9/2006 | Cochrum et al. | |
| 2003/0168756 A1 | 9/2003 | Balkus | |
| 2004/0018226 A1 | 1/2004 | Wnek | |
| 2004/0193088 A1 | 9/2004 | Looney et al. | |
| 2006/0155235 A1 | 7/2006 | Sawyer | |
| 2006/0240110 A1 | 10/2006 | Kiick et al. | |
| 2006/0264130 A1 | 11/2006 | Karles et al. | |
| 2007/0160653 A1 | 7/2007 | Fisher et al. | |
| 2007/0255238 A1 | 11/2007 | Cochrum et al. | |
| 2008/0020015 A1 | 1/2008 | Carpenter et al. | |
| 2008/0021545 A1 | 1/2008 | Reneker et al. | |
| 2008/0265469 A1 | 10/2008 | Li et al. | |
| 2009/0053288 A1 | 2/2009 | Eskridge et al. | |
| 2009/0177272 A1 | 7/2009 | Abbate et al. | |
| 2009/0192214 A1 | 7/2009 | Gravett et al. | |
| 2009/0291124 A1 | 11/2009 | Bedard | |
| 2010/0100123 A1 | 4/2010 | Bennett | |
| 2010/0247614 A1* | 9/2010 | Jiang | A61K 8/368 424/445 |
| 2011/0021964 A1 | 1/2011 | Larsen et al. | |
| 2011/0071498 A1 | 3/2011 | Hakimimer et al. | |
| 2011/0112572 A1 | 5/2011 | Miller | |
| 2011/0125089 A1 | 5/2011 | Senderoff et al. | |
| 2011/0150973 A1* | 6/2011 | Bowlin | A61F 13/00034 424/447 |
| 2011/0250257 A1 | 10/2011 | Arthur et al. | |
| 2013/0095165 A1 | 4/2013 | Olson | |
| 2013/0095229 A1 | 4/2013 | Olson | |
| 2013/0096479 A1 | 4/2013 | Olson | |
| 2013/0280321 A1 | 10/2013 | Olson | |

FOREIGN PATENT DOCUMENTS

| | | |
|---|---|---|
| WO | 2005062880 A2 | 7/2005 |
| WO | 2006/088912 A2 | 8/2006 |
| WO | 2006090150 A1 | 8/2006 |
| WO | 2009042829 A1 | 4/2009 |

OTHER PUBLICATIONS

Jiang et al., "Optimization and Characterization of Dextran Membranes Prepared by Electrospinning", Biomacromolecules, 5(2):326-333 (Mar.-Apr. 2004).
Jiang et al., "Modulation of Protein Release from Biodegradable Core-Shell Structured Fibers Prepared by Coaxial Electrospinning", Journal of Biomedical Materials Research Part B: Applied Biomaterials, 79B(1):50-57 (Oct. 2006).
Notification of Transmittal of the International Search Report and the Written Opinion of the International Searching Authority, or the Declaration (PCT/14/65223) mailed Jan. 29, 2015 (15 pages).
Rothwell et al, "A Salmon Thrombin-Fibrin Bandage Controls Arterial Bleeding in a Swine Aortotomy Model", The Journal of Trauma, 59(1):143-149 (2005).
Extended European Search Report (EP 2,276,879) dated Mar. 27, 2013 (8 pages).
International Search Report and Written Opinion, dated Jan. 29, 2015, 15 pages.

* cited by examiner

*Primary Examiner* — Melissa Javier
(74) *Attorney, Agent, or Firm* — Michael A. Bondi; Moss & Barnett

(57) ABSTRACT

A method of inducing hemostasis in a wound. A hemostatic product is applied to a wound. The hemostatic product includes at least one hemostasis component. The hemostatic product is retained with respect to the wound by positioning a hydrogel material at least partially over the hemostatic product. At least a portion of the hemostatic product is dissolved. Hemostasis is induced in the wound with the at least one hemostasis component. The hydrogel material is separated from the wound. Substantially all of the hemostatic product remains on the wound.

10 Claims, No Drawings

METHOD OF INDUCING HEMOSTASIS IN A WOUND

REFERENCE TO RELATED APPLICATION

This application claims priority to U.S. Provisional Application No. 61/903,100, which was filed on Nov. 12, 2013, the contents of which are incorporated herein by reference.

FIELD OF THE INVENTION

The invention relates generally to products having hemostatic characteristics. More particularly, the invention relates to stabilizers for use in hemostatic products.

BACKGROUND OF THE INVENTION

The body's natural response to stem bleeding from a wound is to initiate blood clotting via a complex process known as the coagulation cascade. The cascade involves two pathways that ultimately lead to the production of the enzyme thrombin, which catalyzes the conversion of fibrinogen to fibrin.

Fibrin is then cross-linked to form a clot, resulting in hemostasis. For wounds that are not severe, and in individuals that have no countervening conditions, the body is usually able to carry out this process efficiently in a manner that prevents excessive loss of blood from the wound. However, in the case of severe wounds, or in individuals in whom the clotting mechanism is compromised, this may not be the case.

For such individuals, it is possible to administer components of the coagulation cascade, especially thrombin and fibrinogen, directly to the wound to bring about hemostasis. Bandaging of bleeding wounds is also a usual practice, in part to isolate and protect the wounded area, and also to provide a means to exert pressure on the wound, which can also assist in controlling bleeding.

While these methods may be carried out satisfactorily in cases of mild trauma or under conditions of "controlled" wounding (e.g. surgery), many situations in which such treatments are most needed are also those in which it is the most difficult to provide them. Examples of such wounds include, for example, those inflicted during combat or unanticipated wounds that occur as the result of accidents. In such circumstances, survival of the wounded individual may depend on stopping blood loss from the wound and achieving hemostasis during the first few minutes after injury. Unfortunately, given the circumstances of such injuries, appropriate medical intervention may not be immediately available.

In particular, the treatment of penetrating wounds such as bullet wounds or some wounds from shrapnel is problematic. This is due to the difficulty in placing a hemostatic product and/or therapeutic agents at the actual site of injury, which includes an area that is well below the body surface and difficult or impossible to access using conventional techniques.

Jiang et al. in Biomacromolecules, v. 5, p. 326-333 (2004) teaches electrospun dextran fibers. Agents associated with the fibers (e.g. BSA, lysozyme) are directly electrospun into the fibers. The fibers may also include other polymers electrospun with the dextran.

Jiang et al. in Journal of Biomedical Materials Research Part B: Applied Biomaterials, p. 50-57 (2006) discloses electrospun fibers that are a composite of poly(ε-caprolactone) as a shell and dextran as a core. These fibers provide the slow release of agents (bovine serum albumin, BSA) that are also electrospun into the fibers.

Smith et al., U.S. Pat. No. 6,753,454, discloses electrospun fibers comprising a substantially homogeneous mixture of a hydrophilic polymer and a polymer that is at least weakly hydrophobic, which may be used to form a bandage. The bandage may comprise active agents (e.g. dextran). However, the disclosed fibers are not readily soluble in liquid.

MacPhee et al., U.S. Pat. No. 6,762,336, teaches a hemostatic multilayer bandage that comprises a thrombin layer between two fibrinogen layers. The bandage may contain other resorbable materials such as glycolic acid or lactic acid based polymers or copolymers. Neither electrospun fibers nor dextran fibers are taught as components of the bandage.

Smith et al., U.S. Pat. No. 6,821,479, teaches a method of preserving a biological material in a dry protective matrix, the matrix comprising fibers such as electrospun fibers. One component of the fibers may be dextran, but homogeneous dextran fibers are not described.

Cochrum et al., U.S. Pat. No. 7,101,862, teaches hemostatic compositions and methods for controlling bleeding. The compositions comprise a cellulose containing article (e.g. gauze) to which a polysaccharide is covalently or ionically crosslinked. The crosslinked polysaccharide may be dextran. However, the compositions are not electrospun and exogenous clotting agents are not included in the compositions.

Wnek et al., U.S. Patent Publication No. 2004/0018226, discloses fibers produced by an electroprocessing technique such as electrospinning The fibers comprise enclosures within the fibers for containing substances that are not miscible with the fibers. Dextran is not taught as a fiber component.

Fisher et al., U.S. Patent Publication No. 2007/0160653, teaches a hemostatic textile comprising hemostatic factors (e.g. thrombin, fibrinogen) but the fibers are formed from electrospun glass plus a secondary fiber (e.g. silk, ceramic, bamboo, jute, rayon, etc.).

Carpenter et al., U.S. Patent Publication No. 2008/0020015, teaches wound dressing comprised of various biodegradable polymers and hydrogels having allogenic or autologous precursor cells (e.g. stem cells) dispersed within the polymers. The polymers may be prepared by electrospinning, and one polymer component may be dextran. However, the polymers cannot be immediately soluble upon contact with liquid, as they must provide a scaffolding for delivery of the cells over time, even though the polymers eventually biodegrade in situ.

Li et al., U.S. Patent Publication No. 2008/0265469, describes electrospun nanofibers that may include dextran. However, the nanofibers are not described as readily soluble in liquids.

Eskridge et al., U.S. Patent Publication No. 2009/0053288, teaches a woven hemostatic fabric comprised of about 65% fiberglass yarn and about 35% bamboo yarn. The fiberglass component may be electrospun, and hemostatic factors such as thrombin may be associated with the fabric, e.g. by soaking the material in a solution of thrombin. This document indicates that dextran may be added as a hygroscopic agent.

There is an ongoing need to provide improved methods and means to initiate blood clotting in wounds to stop or at least slow blood loss. In particular, there is an ongoing need to improve the capability to readily promote hemostasis in severe wounds in a facile manner, especially under circumstances where immediate treatment by medical personnel is limited or unavailable.

Bowlin et al., U.S. Patent Publication No. 2011/0150973, discloses a method of delivering one or more agents of interest to a location of interest. The method includes applying or delivering to a location of interest a hemostatic product. The hemostatic product includes electrospun dextran fibers that dissolve upon contact with liquid. The hemostatic product also includes one or more agents of interest associated with said electrospun dextran fibers. Applying or delivering results in dissolution of the electrospun dextran fibers in liquid at the location of interest to thereby release the one or more agents of interest into the liquid.

SUMMARY OF THE INVENTION

An embodiment of the invention is directed to a method of inducing hemostasis in a wound. A hemostatic product is applied to a wound. The hemostatic product includes at least one hemostasis component. The hemostatic product is retained with respect to the wound by positioning a hydrogel material at least partially over the hemostatic product. At least a portion of the hemostatic product is dissolved. Hemostasis is induced in the wound with the at least one hemostasis component. The hydrogel material is separated from the wound. Substantially all of the hemostatic product remains on the wound.

Another embodiment of the invention is directed to a hemostatic system that includes a hemostatic product and a hydrogel material. The hemostatic product is capable of at least partially dissolving when contacted with a liquid to release hemostasis components from the hemostatic product. The hemostatic products are capable of achieving hemostasis. The hydrogel material is positioned adjacent to at least a portion of the hemostatic product. The hydrogel material is capable of being readily separated from the hemostatic product when the hemostatic product is at least partially dissolved.

Another embodiment of the invention is directed to a method of inducing hemostasis in a wound. A hemostatic product is formed by associating thrombin and fibrinogen with an electrospun dextran support. The hemostatic product is applied to a wound. The hydrogel material is formed by associating at least one hydrophilic polymer with a reinforcing material. The hemostatic product is retained with respect to the wound by positioning a hydrogel material at least partially over the hemostatic product. At least a portion of the hemostatic product is dissolved. Hemostasis is induced in the wound with the thrombin and fibrinogen. The hydrogel material is separated from the wound. Substantially all of the hemostatic product remains on the wound.

DETAILED DESCRIPTION OF THE PREFERRED EMBODIMENTS

An embodiment of the invention is directed to a system for providing hemostasis in a person or animal. The system generally includes a hemostatic product and an applicator material.

The hemostatic product is held in place using the applicator material for a relatively short portion of time over a wound where it is desired to stop the flow of blood from the patient. In certain embodiments, the relatively short period of time is less than about 5 minutes. In other embodiments, the relatively short period of time is about 3 minutes.

When the hemostatic product is applied to the injury site, the materials used to fabricate the hemostatic product dissolve to thereby release the active agents to the injury site and provide the hemostatic effect. The hemostatic product may be used in trauma situations where the condition of the patient must be stabilized until it is possible to transport the patient to a treatment facility that access to medical treatment equipment that is more advanced to the medical treatment equipment available where the patient was injured.

In some embodiments of the invention, only electrospun dextran fibers and the hemostatic agents are used in the hemostatic product and thus after clot formation, there is no need to disturb the clot to remove hemostatic product components, since none remain at the site. The hemostatic product thereby does not leave any residual foreign bodies that elicit foreign body reactions or act as a nidus for infection. Furthermore, the hemostatic product does not contain any xenoproteins, which have the potential of eliciting immune reactions in persons on which the hemostatic product is used.

The components used in fabricating the hemostatic product should be selected to be the same as components found in a living body where the hemostatic product is to be used. Alternatively, the components used in fabricating the hemostatic product are compatible with and readily broken down when the hemostatic product is used on or in a living body. Using such a process minimizes complications associated with components of the hemostatic product not being promptly being broken down as such a process could cause inflammation in the living body. The only thing that remains after the use of the hemostatic product is the clot, which most living bodies are adapted to degrade over time.

The hemostatic system generally includes a hemostatic product having a base to which at least one hemostatic agent is associated. In certain embodiments, the base is fabricated from electrospun dextran and the hemostatic agent is thrombin and/or fibrinogen.

Electrospinning is a non-mechanical processing strategy and can be scaled to accommodate the large volumes necessary to meet the needs of commercial processing. Additional details on the electrospinning process are provided in U.S. application Ser. No. 12/937,322, the contents of which are incorporated herein by reference.

In certain embodiments, the base used in the hemostatic products is formed of substantially homogeneous spun dextran. The amount of dextran used in each hemostatic product can vary depending on the size of hemostatic product that is being manufactured, with typical hemostatic product formulations using from about 5-10 grams of dextran (usually 100,000-200,000 Mr) per hemostatic product.

Of more consequence is the concentration of dextran in the solution from which the fibers are electrospun. Generally, a solution of dextran for electrospinning will be of a concentration in the range of between about 0.1 and about 10 grams per milliliters of solvent. In other embodiments, the dextran concentration is between about 0.5 and about 5 grams per milliliter, and usually such a solution is at a concentration of about 1 gram per milliliter, which is about 0.15 milligrams. A preferred range would be from about 0.9 to about 1.1 grams of dextran per milliliter of solution that is to be electrospun.

The area (length and width) of the hemostatic product of the invention can vary and be adjusted by adjusting spinning parameters. In addition, the mats of dextran fibers can be cut to a desired size after spinning Generally, the hemostatic product will be from about 0.5 centimeters or less to about 30 centimeters or more in length and/or width, but larger or smaller sizes are also contemplated depending on the intended use of the hemostatic system.

Those of skill in the art will recognize that a variety of liquid solvents exist in which it is possible to dissolve dextran. However, superior results for electrospinning dextran are generally achieved when the solvent is water, especially deionized or distilled or deionized, distilled (ddH$_2$O) or other forms of relatively pure water. In addition, there are no negative interactions during use of the hemostatic product associated with water remaining in the hemostatic product and there is far less environmental impact associated with the use of water as compared to many other solvents.

Usually the agents are bioactive agents that have a beneficial or therapeutic effect at the wound site. In one embodiment, the site is a bleeding wound at which it is desired to form a blood clot to stop or slow the bleeding. In this embodiment, the therapeutic substances of interest may include, for example, thrombin and fibrinogen, although other agents active in promoting hemostasis, including but not limited to capscian, may also be included.

The thrombin and/or fibrinogen that are used in the hemostatic product are in forms that are biologically active when they come into contact with blood. Hence upon dissolution, the thrombin acts on the fibrinogen, converting it to fibrin, which then forms a clot within the wound to thereby staunch the flow of blood.

In certain embodiments, the thrombin and fibrinogen may be derived from human sources. In other embodiments, the thrombin and fibrinogen are salmon thrombin and fibrinogen. Advantages of using salmon as a source of these materials include but are not limited to the lack of concern about transmission of etiologic agents (e.g. viruses) that may occur when human and other mammalian sources of thrombin or fibrinogen (e.g. bovine) are used.

The quantity of fibrinogen added to the hemostatic product may be adjusted by changing either the concentration of the fibrinogen in the hemostatic mixture or changing the rate at which the hemostatic mixture is used in the hemostatic product. The quantity of fibrinogen added to the hemostatic product is generally in the range of from about 10 milligrams to about 3 grams. In certain embodiments, the amount of fibrinogen in each of the hemostatic products is between about 20 milligrams to about 1 gram.

The quantity of thrombin added to the hemostatic product may be adjusted by changing either the concentration of the thrombin in the hemostatic mixture or changing the rate at which the hemostatic mixture is used in the hemostatic product. The quantity of thrombin added to each of the hemostatic products is generally between about 10 and 10,000 NIH Units. In certain embodiments, the amount of thrombin in each of the hemostatic products is between about 20 and 6,000 NIH Units.

Association of active agents with the electrospun dextran base may be accomplished by any of many suitable techniques that are known to those of skill in the art, and will depend in part on the precise form of the substance and the means at hand. For example, for powdered, particulate thrombin and fibrinogen, association may be carried out by sprinkling, shaking, blowing, etc. the agents onto a layer of the excipient or carrier.

In some embodiments, active agents such as thrombin may be electrosprayed with sucrose to form sugar droplets, which tends to stabilize thrombin and can also "trap" other substances of interest for delivery to the hemostatic product. In other embodiments, the therapeutic agents may themselves be electrospun. For example, the therapeutic agents are dissolved in and electrospun from a solution. The active agents may be electrospun into other forms such as droplets, beads, etc.

In addition, electrospun or non-electrospun collagen, agents that absorb water, various dry salts that would tend to absorb fluids when placed in contact with e.g. blood; engineered thrombin or thrombin mimics; engineered fibrinogen; agents that cause vasospasm (e.g. ADP, 5-hydroxytryptamine, 5-HT and thromboxane, (TXA-2) to help contract and seal a bleeding vessel, etc. may also be included.

Other components of the clotting cascade may be added to the hemostatic product, for example: tissue factors that are normally only expressed on the surface of damaged cells and that start the normal clotting cascade; serotonin which enhances platelet clumping and promotes vessel constriction; and other agents that are used to replace missing components of the clotting cascade in hemophilia, for example, factor 7 (which activates the so called external extrinsic coagulation cascade) and crude extracts of platelets.

Active agents that function to promote late stages of wound healing may also be included to, for example, facilitate cell migration and remodeling. The incorporation of collagen is an example of such an active agent.

The therapeutic agents must be amenable to drying and are associated with the other components of the hemostatic product in the dry state, since liquid may negatively affect at least one of the components used in the hemostatic product. For example, the active agents may be desiccated or lyophilized, or water may be removed by other means.

In certain embodiments, the electrospun dextran base is placed on a vacuum table, which not only retains the electrospun dextran base in a substantially stationary position during the fabrication process but also causes the hemostatic agents to be drawn into the electrospun dextran base. This process thereby reduces the potential of the hemostatic agent becoming disassociated from the electrospun dextran base while stored in a package as well as when removed from the package prior to applying to the wound.

Depending on the density of the fiber mat, the substances of interest may become relatively evenly dispersed throughout the fiber mat or may be largely confined to the topmost section of the fiber mat. If no backing is present, the latter embodiment is preferable to prevent the particulate substance of interest from falling through and out of the fiber mat.

In another embodiment, a first layer of electrospun dextran may be formed, and one or more of the substances may be associated with the first layer. Then another second layer of electrospun dextran may be formed or placed on top of the substance(s) of interest, and the same or other substances of interest may be associated with the second layer, and so on.

A final or outermost layer of electrospun dextran may be added to prevent the dislodgement of substances of interest from the preceding layer. The number of layers of electrospun dextran that are used in the hemostatic product of the invention may vary widely, from as few as 1-2 to as many as several dozen, or even several hundred, depending on the desired characteristics of the hemostatic product.

Typically, a hemostatic product will contain 1-2 layers. In other embodiments the hemostatic product may include between 2-20 layers. The very slight amount of moisture that is present in a prepared hemostatic product may help to trap and retain the thrombin and fibrinogen on the surface of the hemostatic product.

The height or thickness of the hemostatic product can vary considerably depending on the intended use of the hemostatic product. In certain embodiments, the hemostatic product has a thickness of between about 1 millimeter and about 5 centimeters.

The thickness of the hemostatic product (which is related to the volume) may impact the rate of dissolution of the dextran upon contact with liquid. For example, a thin hemostatic product (e.g. about 2 millimeters) will dissolve more rapidly than a hemostatic product that is thicker, providing the loft of the fibers is comparable.

In most embodiments, dissolution of the dextran fibers is extremely rapid, e.g. about 5 minutes or less after exposure to liquid, or about 4 minutes or less, or about 3 minutes or less, or about 2 minutes or less, or about 1 minute or less. In certain embodiments, the hemostatic product substantially dissolves in between about 1 second and about 20 seconds.

This rapid dissolution may be referred to herein as "instantaneous" or "immediate" dissolution. Compression of an electrospun dextran mat may be used to modulate the rate of dissolution, with greater levels of compression inversely impacting the rate, i.e. generally, the greater the degree of compression, the slower the rate of dissolution.

The rapid rate of dissolution is advantageous, particularly when delivering biologically active agents (e.g. hemostatic agents) to a site of action such as a wound. Rapid dissolution of the carrier dextran fibers provides extremely rapid delivery of the hemostatic agents to the wound upon deployment of the hemostatic product.

Generally, the amount of water that is present in the substances when they are associated with the electrospun dextran fibers is less than about 5%, and preferably less than about 2%. These substances retain full or partial activity when rehydrated, e.g. in blood. Generally, therapeutic substances associated with the hemostatic products of the invention retain, upon contact with liquid, at least about 25%, or about 50%, or even about 75% to 100% of their activity before drying or desiccation, as compared to standard preparations of the substance using standard assays that are known to those of skill in the art.

If thrombin is included in the hemostatic product, it may be desirable to reduce the moisture content of the hemostatic product (e.g. a bandage or gauze) to less than about 5% to preserve thrombin activity during sterilization. This moisture content reduction can be achieved by drying the fabricated hemostatic product, e.g., under a vacuum, or by using a fabrication method that reduces moisture content from the beginning.

To minimize the potential of degradation of the hemostatic product, the hemostatic product should be protected from exposure to moisture because when the components used in the hemostatic product are exposed to moisture, the components degrade such as by dissolving.

The hemostatic product may include one or more stabilizers such as is described in U.S. application Ser. No. 13/622,690, which is assigned to the assignee of the present application and the contents of which are incorporated herein by reference. The stabilizers may enhance the ability of the hemostatic product to dissolve when the hemostatic products are applied to the injury site.

Prior to use of the hemostatic product, it may be desirable for the hemostatic product to be carried by a person on whom the hemostatic product could potentially be used and/or by a person who could potentially use the hemostatic product. In other embodiments, the hemostatic product resists degradation at temperatures of more than 140° F. to less than 0° F.

In certain embodiments, the hemostatic product should resist degradation when exposed to the elevated temperature such as up to about 150° F. for more than about 3 hours. In other embodiments, the hemostatic product should resist degradation when exposed to the elevated temperature for up to about 24 hours.

A threshold for the hemostatic product to be viewed as not experiencing degradation is that the hemostatic product does not exhibit noticeable visible physical changes when viewing the hemostatic product without magnification. The hemostatic product should also not experience noticeable physical changes when the hemostatic product is examined with magnification such as with a magnifying glass or a microscope.

The preceding characteristics should be displayed by the hemostatic product regardless of whether the hemostatic product is retained in the packaging materials while exposed to the elevated temperature conditions.

The stabilizer also enhances the usable shelf life of the hemostatic product. In certain embodiments, the stabilizer provides the hemostatic product with a shelf life of at least about 2 years. In other embodiments, the hemostatic product exhibits a shelf life of at least 3 years. As used herein, the term usable shelf life means that the hemostatic product does not exhibit noticeable degradation when viewed without magnification or with magnification such as a magnifying glass or microscope.

In some embodiments of the invention, the hemostatic products also include one or more support structures or support materials incorporated therein. For example, a backing may be incorporated into the hemostatic product.

The support material may be formed from various electrospun materials such as polyglycolic acid (PGA), polylactic acid (PLA), and their copolymers (PLGAs); charged nylon, etc. In one embodiment, the support material is compressed electrospun dextran fibers. By "compressed electrospun dextran fibers," it is meant that electrospun dextran fibers are compressed together under pressure.

The support material may or may not be soluble in liquid, or may be slowly soluble in liquid, and may or may not be permeable to liquid. Slowly soluble materials include those from which absorbable or dissolving (biodegradable) stitches or sutures are formed, included PGA, polylactic and caprolactone polymers.

In certain embodiments, the support material may dissolve relatively quickly such as less than about 1 hour. In other embodiments, the support material may dissolve within from about 10 days to 8 weeks. In either case, the support material provides the advantage of not having to remove the hemostatic product and risk disrupting the clot.

However, in any case, the support material should not interfere with the immediate dissolution of the hemostatic product and delivery of the active agents associated therewith into the liquid that dissolves the hemostatic product.

All such arrangements, shapes, and embodiments of carrier layers and support materials as described herein are intended to be encompassed by the invention.

The hemostatic product may be sterilized prior to use, generally by using electromagnetic radiation, for example, X-rays, gamma rays, ultraviolet light, etc. Typically, the hemostatic products are sterilized using X-rays in a dose of about 5 kilograys (kGray). Any method that does not destroy the carrier or the activity of substances associated with the fibers may be used to sterilize the hemostatic products of the invention.

The hemostatic product may also include diagnostic agents that can be used by the treating medical professional to diagnose the nature of the injury. In certain embodiments, the diagnostic agent may change colors to indicate the presence of particular chemicals in the blood or to indicate particular characteristics of the blood. For example, if the patient is currently taking medications that cause thinning of the patient's blood. The diagnostic agents could also change colors to indicate the oxygen and/or glucose level of the blood.

In other embodiments, the products of the invention need not comprise agents that promote clotting at all. Those of skill in the art will recognize that the products of the invention are highly suitable for delivering many substances of interest to a desired liquid environment or location. For example, the products may be designed for delivery of therapeutic or beneficial substances to any moist environment of the body, where there is sufficient liquid to dissolve the electrospun dextran fibers and release the active substance, and where dissolved dextran is not problematic.

Such substances may include, for example, enzymes or their precursors (e.g. pro-enzymes or zymogens) and their substrates, substances that activate a protein or enzyme (e.g. proteases, cofactors, etc.), and the like.

For example, hemostatic products comprised of only thrombin might be used for small injuries or in combination with other interventions. In addition, other therapeutically beneficial substances may also be associated with the hemostatic product, including but not limited to: antibiotics, antiviral agents, anti-helminthic agents, anti-fungal agents, medicaments that alleviate pain, growth factors, bone morphogenic protein, vasoactive materials (e.g. substances that cause vasospasms), steroids to reduce inflammation, chemotherapy agents, contraceptives, etc.

Examples include but are not limited to oral, nasal, tracheal, anal, lung, and vaginal delivery of substances such as anti-microbial agents, analgesic agents, nutritional agents, etc. Oral applications include the delivery of substances useful for dental treatments, e.g. antibiotics, pain medications, whitening agents, etc.

In some embodiments, no bodily fluid is present (or if insufficient body fluid is present) and the applied hemostatic product can be "activated" by wetting, e.g. by spraying, or by otherwise applying a source of moisture (e.g. by exposing the hemostatic product to a moist material such as a sponge), or dropping hemostatic products into a liquid (e.g. a body of water), to cause release of the agents of interest associated with the dextran fibers.

The electrospun dextran fiber hemostatic products of the invention may serve as a "scaffolding" or carrier for containing, storing and/or transporting the substance(s) until use, i.e. until contacted with liquid that dissolves the electrospun dextran fibers, concomitantly releasing the substances into the liquid. Such substances may include, for example, enzymes or their precursors (e.g. pro-enzymes or zymogens) and their substrates, substances that activate a protein or enzyme (e.g. proteases, cofactors, etc.), and the like.

One of the challenges in successfully treating a wound, especially a wound where there is significant blood flow, is to achieve hemostasis. In addition to applying a hemostatic product such as is described in the other portions of this patent application, pressure is applied to the wound to enhance the likelihood that hemostasis will be achieved.

In certain embodiments, the pressure is provided by direct manual pressure such as using a human hand. In other embodiments, a material is placed over the wound and the direct manual pressure is used to hold the material in place.

The material may have absorbent capabilities such that blood and other fluids that are in proximity to the material are absorbed into the material. In such situations, it is possible for the clot to become associated with the material such as on the surface of the material or at least partially in the matrix of the material.

As the pressure that is applied either solely with manual force or in conjunction with the additional material is removed, it is important to minimize disruption of the clots that caused the hemostasis to be achieved. Such disruption can cause bleeding to resume, which disrupts the healing process.

Separation of the material used to apply the pressure from the wound area is complicated by the fact that especially when just formed, the clots can be relatively sticky. Additionally, the components used in the hemostatic products described herein such as thrombin and fibrinogen can also be relatively sticky after being dissolved by contact with a liquid such as blood.

It has been found that the ability to achieve hemostasis through the use of applying pressure and the ability to separate the object used to apply the pressure from the area in which hemostasis has been achieved is enhanced by the use of a hydrogel product intermediate the object used to apply the pressure and the area in which it is desired to achieve hemostasis.

The hydrogel may be provided in a variety of forms using the concepts of the invention. In one such embodiment, the hydrogel is provided in a sheet. The hydrogel sheet may be formed with a length and a width that are greater than the length and the width of the wound to thereby facilitate achieving hemostasis over substantially all of the wound at substantially the same time. In other embodiments, the hydrogel sheet facilitates achieving hemostasis of the entire wound at the same time.

In situations where the wound has a length and/or a width that are greater than the length and/or width of the hydrogel sheet, multiple hydrogel sheets can be used to cover substantially all of the wound to facilitate causing substantially complete hemostasis of the wound.

In other situations where the wound has a length and/or a width that are greater than the length and/or width of the hydrogel sheet, the hydrogel sheet may be held in place over a portion of the wound. Once hemostasis is achieved over this portion, the hydrogel sheet can be repositioned to provide hemostasis of another portion of the wound. This process is repeated until hemostasis has been provided over the entire wound.

The hydrogel sheet includes at least one hydrophilic polymer that has been approved for use in medical applications. In certain embodiments, the hydrogel sheet includes at least one hydrophilic polymer selected from the following group.

The hydrogel sheet includes a relatively high water concentration. In certain embodiments, the water concentration in the hydrogel sheet is greater than about 70 percent. In other embodiments, the water concentration in the hydrogel sheet is greater than about 80 percent. In still other embodiments, the water concentration in the hydrogel sheet is about 95 percent.

In addition to the preceding hydrogel components, the hydrogel sheet may include a reinforcing material that increases the structural integrity of the hydrogel sheet and thereby enhances the ability to manipulate the hydrogel sheet without damage thereto such as portions of the hydrogel sheet becoming dislodged.

In certain embodiments, the reinforcing material has a mesh configuration with a plurality of openings formed therein. The openings enables hydrogel placed on opposite sides of the reinforcing material to join together through the reinforcing material. An example of one such hydrogel material is a nylon scrim.

In other embodiments, the reinforcing material is a backing material that is attached to a side of the hydrogel sheet that is opposite the wound. To enhance the ability of the hydrogel sheet to remain in attachment with the reinforcing material, the backing material may include pores that are adapted to receive the hydrogel. These pores may be similar to the openings discussed in the preceding paragraph. However, a difference between the reinforcing material discussed in the preceding paragraph and the backing material discussed in this paragraph is that the hydrogel material cannot be contacted on the side of the backing material that is opposite the hydrogel sheet that is in contact with the wound.

The backing material may include features that assist in identifying the location of the hydrogel pad. These features also encourage persons who are treating the person with the wound to remember to remove the hydrogel pad after an appropriate period of time.

In certain embodiments, the backing material may be formed with a color that contrasts from the color of the person's skin as well as the color of blood. For example, the backing material may be formed with a green or blue color.

Alternatively or additionally, the backing material includes a design printed thereon that enhances the ability to identify the location of the hydrogel layer. An example of the design is a plurality of lines that are arranged in an array such as diamonds or squares. The design may be provided in a color that enhances the ability to see this design that thereby identifies the backing material and the associated hydrogel layer.

Alternatively or additionally, the backing material includes text that advises the person applying the hydrogel sheet to remove the hydrogel sheet. Depending on the intended use of the hydrogel sheet, the text may be a general warning or may provide a specific duration in which the hydrogel sheet is to remain on the wound.

In the embodiment of the hydrogel sheet that includes the reinforcing material at an intermediate location thereof, a release layer may be provided over the surface of the hydrogel sheet that is opposite the side of the hydrogel sheet that is in contact with the wound.

The release layer is intended to remain in contact on the hydrogel sheet during use of the hydrogel sheet in conjunction with achieving hemostasis. The release layer should resist separation from the hydrogel sheet such as when the hydrogel sheet is removed from the wound after hemostasis has been achieved or when it is desired to replace the hydrogel sheet or another component that is used in conjunction with achieving hemostasis. Similar to backing material, the release layer may include features that enhance the ability to see the release layer and the associated hydrogel sheet.

To facilitate handling of the hydrogel sheet prior to use, it may be advantageous to provide a release layer on the side of the hydrogel sheet that is placed adjacent to the wound. In contrast from the release layer that is applied to the side of the hydrogel sheet that is opposite wound, the release layer that is applied to the wound side of the hydrogel sheet can facilitate readily separating this release layer from the hydrogel sheet prior to applying the hydrogel sheet to the wound.

In use, the hemostasis product is applied to the wound and then the hydrogel sheet is placed over the hemostasis product. Pressure is applied to the hydrogel sheet and such pressure causes the hemostasis product to engage the wound for a period of time to promote the hemostasis. In certain embodiments, the period of time is up to about 5 minutes. In other embodiments, the period of time is between about 2 minutes and about 3 minutes.

During the time in which the hydrogel sheet is placed over the wound, at least a portion of the hemostasis product dissolves into and/or around the wound. Dissolving causes the components in the hemostasis product such as thrombin and fibrinogen to be released into the wound and thereby cause hemostasis.

Thereafter, the hydrogel sheet is removed from over the wound. In certain situations, substantially all of the hemostasis product has dissolved by the time the hydrogel sheet is removed from the wound. In other situations, a portion of the hemostasis product remains undissolved when the hydrogel sheet is removed from the wound.

The wound is then reviewed to determine if a desired amount of hemostasis has been achieved. If a desired amount of hemostasis has not been achieved, the hydrogel sheet is placed over the wound. Pressure is applied to the hydrogel sheet for an additional period of time. In certain embodiments, the additional period of time is up to about 5 minutes. In other embodiments, the additional period of time is between about 2 minutes and about 3 minutes.

In other embodiments where bleeding is significant after the hydrogel sheet is removed and a substantial portion of the hemostasis product has dissolved, another hemostasis product is placed over the wound prior to the hydrogel sheet being reapplied on the wound. This process can be repeated until a desired level of hemostasis has been achieved. Each time the hydrogel sheet is separated from the wound, the at least partially solidified components in the wound such as clots and the undissolved portions of the hemostasis product remain associated with the wound instead of being associated with the hydrogel product such that separation of the hydrogel sheet from the wound does not cause such materials to be pulled away from the wound by the hydrogel sheet.

The hydrogel sheet can include a radiopaque marker that can be used to determine if the hydrogel sheet using an imaging technique such as x-ray imaging. The radiopaque marker may be incorporated into or otherwise associated with at least one of the reinforcing material and the backing material.

In certain embodiments, the radiopaque marker includes at least one thread that is fabricated from a radiopaque material. Because the hydrogel sheet is used in conjunction with a wound in a patient, the material from which the radiopaque marker is fabricated should not cause negative interactions when coming into contact with the patient. Additionally, the radiopaque marker should not exhibit degradation from contact with tissue and/or fluids in or around the wound. An example of one such material that exhibits radiopaque characteristics is titanium.

Alternatively or additionally, a radiopaque coating may be applied to at least one of the reinforcing material and the backing material. Examples of materials that exhibit biocompatibility that can be used in the radiopaque coating include gold, platinum, iridium, palladium, and rhodium.

In another embodiment of the invention, the fibrinogen and thrombin are applied to a surface of or incorporated into an applicator. Such an applicator enables the fibrinogen and thrombin to be accurately delivered to an area where hemostasis is desired.

In one such configuration, the applicator has an elongated portion that may be grasped by a person who is using the hemostatic product. The applicator may have a configuration that is similar to a swab. This configuration of the hemostatic product is particularly suited for locations that are difficult to directly reach. An example of one such condition that this hemostatic product may be used to treat is epistaxis.

At least one of the fibrinogen and thrombin may be electrospun either alone or with another component such as dextran. The fibers produced using such a process may be wrapped around a distal end of the applicator.

The applicator may be configured to release the fibrinogen and thrombin once the hemostatic product encounters blood. Using such a process, the fibrinogen and thrombin would cause clots to form. The clots could be removed from the patient. If the clots are sufficiently small, the clots may be allowed to remain in the patient such that the clots could eventually be broken down.

In another configuration of this hemostatic product, at least one of the fibrinogen and thrombin may be configured to remain relatively close to or be confined to the applicator such that when the fibrinogen and thrombin cause at least one clot to form, such clots remain attached to the applicator. This configuration facilitates removal of the clots from the patient and may be desirable where the clots are likely to be sufficiently large to make it undesirable for the clots to remain in the body.

To facilitate the fibrinogen and thrombin not being released from the applicator, the fibrinogen and thrombin may be incorporated into a material that is attached to an end of the applicator. An example of one such material is foam. The foam may be either open cell foam or closed cell foam.

The foam should have pores that are sufficiently large to receive the fibrinogen and thrombin. The foam should not have a strong affinity for either fibrinogen or thrombin so that when the fibrinogen and thrombin are exposed to water, these components are released from the foam.

In another configuration of the applicator, the thrombin, fibrinogen and other components used in fabricating the hemostatic device are positioned on the location in which hemostasis is desired. The applicator is placed over the hemostatic device to thereby hold the hemostatic device in position while the thrombin and fibrinogen produce clotting.

A surface of the applicator that is adjacent to the thrombin and fibrinogen should resist sticking to the thrombin and fibrinogen as well as to the clot that is caused by the thrombin and fibrinogen and the other portions of the tissue that is bleeding.

Using such a configuration minimizes the potential that the clot will be separate from the tissue when the applicator is removed. Separation of the clot from the tissue is undesirable because it could cause bleeding to resume.

Separating the applicator from the thrombin and fibrinogen is complicated by the fact that these components tend to become sticky when in contact with liquid such as water or blood.

The applicator thereby enhances the ability to apply pressure of substantially the entire area of the thrombin and fibrinogen as well as the area of the tissue that is bleeding. This pressure enhances the likelihood that the hemostatic device will produce substantially complete hemostasis.

A surface of the applicator that is in contact with the thrombin and the fibrinogen may be at least partially covered with a material that reduces the potential of the thrombin, the fibrinogen, the clot and the adjacent tissue remaining in contact with the applicator when it is desired to remove the applicator. An example of one such applicator coating material is a hydrogel.

While it is desired for the applicator coating material to not stick to the thrombin, the fibrinogen, the clot and the adjacent tissue, in certain embodiments, it is desired for the applicator coating material to remain affixed to the applicator when the applicator is removed from the tissue.

An example of one suitable technique for attaching the applicator coating material to the applicator is a mechanical fastener such as a screw that extends through an aperture in the applicator coating material and engages the applicator.

In certain embodiments, the applicator coating material is permanently attached to the applicator so that both of these components are discarded after use. In other embodiments, the applicator coating material is removably attached to the applicator. After use, the applicator coating material is separated from the applicator. This configuration enables the applicator to be reused.

In addition to being used to produce hemostasis in humans, the concepts of the invention may be adapted for use in conjunction with other animals. Examples of such animals on which the invention can be used include dogs and cats.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of inducing hemostasis in a wound comprising:
applying a hemostatic product to a wound that is bleeding, wherein the hemostatic product comprises at least one hemostasis component;
retaining the hemostatic product with respect to the wound by positioning a hydrogel material at least partially over the hemostatic product and applying pressure to the hemostatic product with the hydrogel material;
dissolving at least a portion of the hemostatic product;
inducing hemostasis in the wound with the at least one hemostasis component to form a clot; and
separating the hydrogel material from the wound so that disruption of the clot is minimized and the wound does not resume bleeding, wherein substantially all of the hemostatic product remains on the wound.

2. The method of inducing hemostasis of claim 1, wherein the hemostatic product comprises an electrospun dextran support on which the at least one hemostasis component is associated, wherein the at least one hemostasis component comprises at least one of thrombin and fibrinogen.

3. The method of inducing hemostasis of claim 1, wherein the hydrogel material comprises:
   at least one hydrophilic polymer; and
   a reinforcing material to which the hydrophilic polymer is associated.

4. The method of inducing hemostasis of claim 3, wherein reinforcing material comprises mesh.

5. The method of inducing hemostasis of claim 1, and further comprising associating a backing material with the hydrogel material.

6. The method of inducing hemostasis of claim 5, wherein the backing material has plurality of pores formed therein and wherein the pores receive the hydrogel material.

7. The method of inducing hemostasis of claim 5, wherein the backing material has at least one identifying feature that is distinct from the hemostatic product and wherein the at least one identifying feature comprises color, text, design or combination thereof.

8. The method of inducing hemostasis of claim 1, wherein the hemostatic product and the hydrogel material are both provided in a sheet.

9. A method of inducing hemostasis in a wound comprising:
   providing a hemostatic product comprising thrombin and fibrinogen associated with an electrospun dextran support;
   applying the hemostatic product to a wound that is bleeding;
   providing a hydrogel material comprising at least one hydrophilic polymer associated with a reinforcing material;
   retaining the hemostatic product with respect to the wound by positioning the hydrogel material at least partially over the hemostatic product and applying pressure to the hemostatic product with the hydrogel material;
   dissolving at least a portion of the hemostatic product;
   inducing hemostasis in the wound with the thrombin and fibrinogen to form a clot; and
   separating the hydrogel material from the wound so that disruption of the clot is minimized and the wound does not resume bleeding, wherein substantially all of the hemostatic product remains on the wound.

10. The method of inducing hemostasis of claim 9, wherein the backing material has plurality of pores formed therein and wherein the pores receive the hydrogel material.

* * * * *